United States Patent
Chen et al.

(10) Patent No.: US 10,393,637 B2
(45) Date of Patent: Aug. 27, 2019

(54) SAME TIME DOMAIN MULTI-FREQUENCY BAND HYDRAULIC TESTING SYSTEM AND CONTROL METHOD THEREFOR

(71) Applicant: Chang-Sha Dayonchuan Electromechanical Technology Co., Ltd, Chang Sha (CN)

(72) Inventors: Lidan Chen, Chang Sha (CN); Hong Chen, Chang Sha (CN)

(73) Assignee: CHANGSHA DAYONCHUAN ELECTROMECHANICAL TECHNOLOGY CO., LTD., Changsha, Hunan (CN)

(*) Notice: Subject to any disclaimer, the term of this patent is extended or adjusted under 35 U.S.C. 154(b) by 294 days.

(21) Appl. No.: 15/324,273

(22) PCT Filed: Apr. 8, 2015

(86) PCT No.: PCT/CN2015/076045
§ 371 (c)(1),
(2) Date: Apr. 19, 2017

(87) PCT Pub. No.: WO2016/004778
PCT Pub. Date: Jan. 14, 2016

(65) Prior Publication Data
US 2017/0248504 A1 Aug. 31, 2017

(30) Foreign Application Priority Data
Jul. 8, 2014 (CN) .......................... 2014 1 0322918

(51) Int. Cl.
*G01N 3/10* (2006.01)

(52) U.S. Cl.
CPC ..................................... *G01N 3/10* (2013.01)

(58) Field of Classification Search
CPC ....................................................... G01N 3/10
See application file for complete search history.

(56) References Cited

U.S. PATENT DOCUMENTS

| 6,402,089 B1* | 6/2002 | Kiss ...................... B64C 27/001 181/207 |
| 2015/0224845 A1* | 8/2015 | Anderson ............ B60G 17/019 701/37 |

* cited by examiner

*Primary Examiner* — Manuel A Rivera Vargas
(74) *Attorney, Agent, or Firm* — Raymond Y. Chan; David and Raymond Patent Firm

(57) ABSTRACT

A same-time-domain multi-frequency band hydraulic system, comprising a high-frequency data processing system, a control system, an executive system, a load, a static measuring system, and a dynamic measuring system, wherein the high-frequency data processing system processes the input command signals, data from the dynamic measuring system, and data from the static measuring system, and automatically generates, displays, and saves same-time-domain multi-frequency band test result data, wherein part of input signals are converted into input signals of the control system by the high-frequency data processing system and executed by the executive system, wherein the frequency response and measurement accuracy of the dynamic measuring system and the front-end data processing system meet the requirements of both the test and the hydraulic testing system.

2 Claims, 1 Drawing Sheet

SAME TIME DOMAIN MULTI-FREQUENCY BAND HYDRAULIC TESTING SYSTEM AND CONTROL METHOD THEREFOR

NOTICE OF COPYRIGHT

A portion of the disclosure of this patent document contains material which is subject to copyright protection. The copyright owner has no objection to any reproduction by anyone of the patent disclosure, as it appears in the U.S. Patent and Trademark Office patent files or records, but otherwise reserves all copyright rights whatsoever.

BACKGROUND OF THE PRESENT INVENTION

Field of Invention

The present invention relates to a hydraulic testing system in the field of electromechanical control, and, in particular, to a same-time-domain multi-frequency band hydraulic testing system and control method thereof.

Description of Related Arts

A conventional complete hydraulic testing system, according to the block schematic diagram, is formed of five portions, which are data processing system, control system, executive system, load, and measuring system. Input command signal is identifiable computer program language translated from the test plan for the hydraulic testing system. The input command signal is utilized for commanding the acts of the hydraulic testing system. The data processing system processes the input command signal and data from the measuring system and commands the acts of the control system. The control system in the hydraulic system control and adjust the pressure, current capacity, and direction of the fluid. The executive system converts the pressure energy of the fluid into mechanical energy to drive the load to conduct straight line reciprocal motion or rotation. The load is the response of the hydraulic testing system and usually is the response of the test subject to the input command signal. The measuring system is to measure the response of the hydraulic testing system and to serve as feedback. The minimum frequency of hydraulic system ($f_{min}$) is the control frequency that is usually determined by the frequency characteristics of the electrohydraulic servo valve of the control system. Besides, the test frequency and data processing frequency of the hydraulic system may both be higher than the control frequency of the system ($f_{min}$). A hydraulic testing system mainly includes two parts, which are hydraulic system and test subject. When the testing system is utilized in the field of civil engineering, if a compression and tensile test is conducted on concrete, high-strength concrete, and ultra-high strength concrete, it usually obtains a stress-strain curve, while if a stress-strain complete process curve (complete curve hereinafter) test is conducted on rock, high-strength concrete, and ultra-high strength concrete, a complete curve is usually expected to be obtained. Stress-strain curve and complete curve are two of the most basic characteristic curves to research materials mechanics properties. It can even apply the law of conservation of energy to analyze the interrelations among the stress-strain curve, the complete curve, and the hydraulic testing system. Stress-strain curve test and complete curve test are usually independently completed in a hydraulic testing system. Because brittle failure occurs on concrete, especially high-strength concrete and ultra-high strength concrete in compression and tensile test, but the measurement frequency of the measuring system in the hydraulic testing system (static measuring system hereinafter) is not high enough, the full view of the characteristics of the stress-strain curve and complete curve can not be adequately described. Some adds a dynamic stress strain measuring system (dynamic measuring system hereinafter) besides the conventional hydraulic testing system to independently collect data. Then the stress-strain curve or complete curve can be obtained by the data processing afterward. Unfortunately, because the dynamic measuring system and the hydraulic testing system are two independent systems, the dynamic measuring system can not feedback for the controlling of the test and the data processing afterward can not guarantee enough accuracy as well.

A complete hydraulic testing system, according to its composition and structure, is formed of six portions, which are power system, data processing system, control system, executive system, auxiliary system, and hydraulic fluid. The power system turns the mechanical energy of the prime motor into the pressure energy of the fluid. The data processing system processes the input command signal and data from the measuring system and commands the acts of the control system. The control system controls and adjusts the pressure, current capacity, and direction of the fluid in the hydraulic system. The executive system converts the pressure energy of the fluid into mechanical energy to drive the load to conduct straight line reciprocal motion or rotation. The auxiliary system mainly comprises the fuel tank, oil filter, oil tube and pipe connector, sealing ring, quick change connector, etc. The hydraulic fluid is the actuating medium that transmits energy in the hydraulic system. The minimum frequency of hydraulic system ($f_{min}$) is the control frequency that is usually determined by the frequency characteristics of the electrohydraulic servo valve of the control system. Besides, the test frequency and data processing frequency of the hydraulic system may both be higher than the control frequency of the system ($f_{min}$). The opening of the valve of the control system has two types in terms of continuity, which are two states (completely opened and completely closed) and continual opening. The description of degree of valve opening can be in two ways, which are in relative value and in absolute value. For example, the valve opening of the completely closed state is zero for both descriptions of relative value and absolute value, while the valve opening of the completely opened state is 100% in relative value and 1, 100, or other positive integer greater than 100 in absolute value.

When hydraulic system suddenly starts, stops, changes speed, or reverses, the valve port will suddenly close or stop. Nonetheless, because of the inertia of the flowing fluid and moving parts, there will be a very high peak pressure instantly generated in the system, which phenomenon is called hydraulic impact. When hydraulic impact occurs, the peak value of the partial pressure change in the system may reach several times of the regular functioning pressure value. Therefore, it is extremely likely to render vibration of the system and possibly to cause seal breakage, pipeline burst, or weld line crack that trigger oil leakage in the system. Besides, it can bring manometer and flowmeter fail, pressure relay and sequence valve misssend signal, pressure regulating valve and flow valve break. Moreover, it may even lead the load of the concrete sample (component) to attain the ultimate load and scrap the sample (component). Hydraulic impact not only influences the reliability of the hydraulic system itself, but also cracks or scraps the concrete sample (component) or possibly causes secondary impact to the personnel and environment.

The limitations of conventional hydraulic testing system includes:

1. Because the measurement frequency of the measuring system in the conventional hydraulic testing system is not high enough, when a hydraulic testing system is solely employed to conduct a stress-strain curve test and a complete curve test, it can not fully describe the characteristics of the stress-strain curve and complete curve. Adding a dynamic measuring system outside of a conventional hydraulic testing system to independently collect data is another option. Unfortunately, because the dynamic measuring system and the hydraulic testing system are two independent systems, the dynamic measuring system can not feedback for the controlling in the test and the data processing afterward can not guarantee enough accuracy as well.

2. Conventional hydraulic impact preventions and treatments are mostly focusing on providing physical improvements of the power system, control system, executive system, auxiliary system, and hydraulic fluid of the hydraulic system, while there is still not enough improvement on control method and the hydraulic impact problem is not completely solved yet.

SUMMARY OF THE PRESENT INVENTION

For the above drawbacks of prior art, an object of the present invention is to provide a comprehensive control method of same-time-domain multi-frequency band hydraulic testing system that, on the basis of conventional hydraulic testing system, replaces original data processing system by high-frequency data processing system, add a dynamic measuring system, and utilizes a control method of same-time-domain multi-frequency band hydraulic testing system, so as to raise the overall level of the stress-strain curve test and the complete curve test. The control is based on the loading load (loading hereinafter) speed required by the hydraulic test, the actual measured loading speed of the hydraulic system (v), and acceleration (a) and the additional maximum acceleration ($a_{max}$). Besides, the maximum acceleration ($a_{max}$) can accommodate to a loading way of segment increment, which can prevent the occurrence of hydraulic impact. Therefore, it enhances the reliability of the hydraulic system itself, prevents the concrete sample (component) from cracking or scraping, and avoids secondary impact to the personnel and environment, so as to raise the reliability and efficiency of the entire system. In addition, the high-frequency data processing system can be utilized to conduct high speed computing to the data of the static measuring system, which enhances the speed of response of the entire system to the load feedback and further improves the preventive effect against hydraulic impact.

In order to achieve the above objects, a technical solution according to the present invention is a same-time-domain multi-frequency band hydraulic system, comprising a high-frequency data processing system, a control system, an executive system, a load, a static measuring system, and a dynamic measuring system. The static measuring system and the dynamic measuring system real time monitor the operation of the load. The high-frequency data processing system processes the input command signals, data from the dynamic measuring system, and data from the static measuring system, and automatically generates, displays, and saves same-time-domain multi-frequency band test result data. Part of input signals are converted into input signals of the control system by the high-frequency data processing system and executed by the executive system. The frequency response and measurement accuracy of the dynamic measuring system and the front-end data processing system should meet the requirements of both the test and the hydraulic testing system.

A control method utilizing the above hydraulic system to conduct hydraulic test, comprising the following steps:

(1) setting up the factor of the initial period for loading (k) of the hydraulic system and calculating the initial period for loading ($t_c$) of the hydraulic system according to the operating performance of the hydraulic testing system, loading speed required by the test ($v_y$), and the control frequency ($f_{min}$) of the hydraulic system, wherein k is a positive integer greater than or equal to 2.

(2) calculating the maximum acceleration ($a_{max}$) of the initial loading based on the loading speed required by the test ($v_y$) and the initial period for loading (tc) of the hydraulic system in the step (1), wherein regarding the loading speed required by the test ($v_y$) and the maximum acceleration ($a_{max}$), during the loading process of the hydraulic test, the hydraulic system simultaneously satisfies that the actual loading velocity (v) is equal to the loading speed required by the test ($v_y$) and that the actual loading acceleration (a) is less than or equal to the maximum acceleration ($a_{max}$); and (3) applying the loading way of segment increment to the maximum acceleration ($a_{max}$) in the initial loading phase of the hydraulic system, wherein the number of segment (i) is a positive integer of 2 or 3, wherein the actual loading velocity ($v_i$) that controls each phase is equal to the loading speed required by the phase ($v_{yi}$), wherein the actual loading acceleration (ai) is less than or equal to the maximum acceleration of that phase ($a_{maxi}$).

Furthermore, the high-frequency data processing system conducts high speed computing and processing according to the control method for the hydraulic system to launch a hydraulic test with the signal input thereby, which can further eliminate the hydraulic impact.

Contrasting to prior art, advantages of the present invention comprise that on the basis of conventional hydraulic testing system, original data processing system has been replaced by high-frequency data processing system, a dynamic measuring system is added, and a control method of same-time-domain multi-frequency band hydraulic testing system is utilized, which raises the overall level of the stress-strain curve test and the complete curve test. The control is based on the loading speed required by the hydraulic test ($v_y$), the actual measured loading speed of the hydraulic system (v), and acceleration (a) and the additional maximum acceleration ($a_{max}$). Besides, the maximum acceleration ($a_{max}$) can accommodate to a loading way of segment increment, which can prevent the occurrence of hydraulic impact. In addition, the high-frequency data processing system can be utilized to conduct high speed computing to the data of the static measuring system, which enhances the speed of response of the entire system to the load feedback and further improves the preventive effect against hydraulic impact.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

The following employs the drawings to further describe the embodiment according to the present invention.

Figure 1:
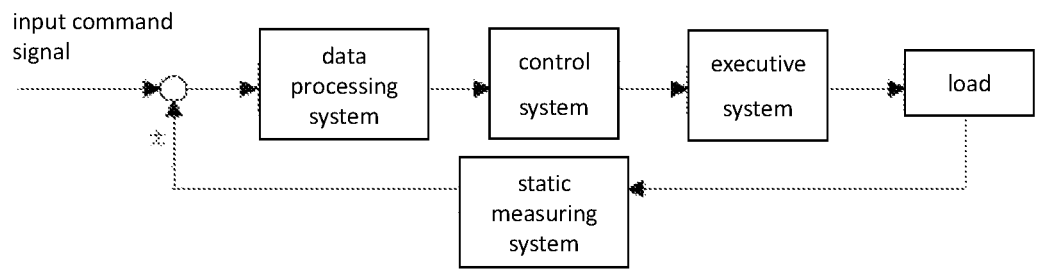
FIG. 1 is a block diagram of the hydraulic testing system according to prior art.
Figure 2:
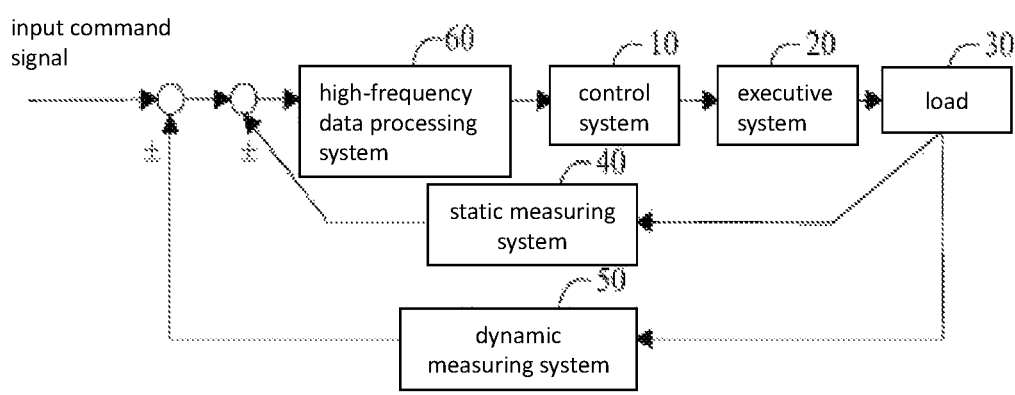
FIG. 2 is a block diagram of a same-time-domain multi-frequency band hydraulic testing system according to the present invention.

Referring to FIG. 2, a same-time-domain multi-frequency band hydraulic testing system comprises a high-frequency data processing system 60, a control system 10, an executive system 20, a load 30, a static measuring system 40, and a dynamic measuring system 50. The frequency response and measurement accuracy of the dynamic measuring system and the front-end data processing system should be able to satisfy the requirements of both the test and the hydraulic testing system.

The high-frequency data processing system 60 will process the input command signals, data from the dynamic measuring system, and data from the static measuring system and automatically generate, display, and save the same-time-domain multi-frequency band hydraulic test result data. Because static measuring system has better stability and higher accuracy then dynamic measuring system in low frequency, part of the data of the static measuring system will be processed by the high-frequency data processing system 60 and converted into input signals of the control system 20 for the executive system 20 to conduct the test of the sample.

First Embodiment

The controlled object of the control method for advance prevention of the hydraulic impact is the load:

A 500 ton electrohydraulic servo pressure testing machine. The control frequency of the system ($f_{min}$) is 150 Hz. The loading speed required by the test ($v_y$) is 18.0 kN/s. The maximum valve opening is 30000. The testing machine will be suspended and the load will be reset after the testing machine starts and the cylinder arrives the position where the test item is 2 mm from the top board. When a regular hydraulic test starts, the automatic conversion program will be launched first, so as to ensure slow loading of the cylinder. The valve opening of the initial loading controlled by the computer is 1000. When the load is 1000N, the computer controlled system will automatically switch to that the actual loading speed (v) to be equal to loading speed required by the test ($v_y$), simultaneously satisfy that the acceleration of the actual loading (a) is lower than or equal to the maximum acceleration ($a_{max}$), set the initial velocity of the cylinder ($v_0$) to be equal to 0 and the factor of the initial period for loading of the hydraulic system (k) to be equal to 30000, and utilize three speed 20/30/50 incremental control on the maximum acceleration of the hydraulic system ($a_{max}$).

According to the above test conditions, because the control frequency period ($T_{min}$) is:

$$T_{min}=1/f_{min}(s) \quad (1)$$

the initial period for loading (tc) of the hydraulic system is:

$$t_c=k\times T_{min}=k\times(1/f_{min})=k/f_{min}=30000/150=200(s) \quad (2)$$

Assuming that under the uniform acceleration of the hydraulic system, the initial first, second, and third time periods are respectively $t_{c1}$, $t_{c2}$, and $t_{c3}$, then:

$$t_{c1}=t_c\times5/10=200\times5/10=100(s) \quad (3)$$

$$t_{c2}=t_c\times3/10=200\times3/10=60(s) \quad (4)$$

$$t_{c3}=t_c\times2/10=200\times2/10=40(s) \quad (5)$$

Assuming the final speed of the initial first, second, and third stages are respectively $v_1$, $v_2$, and $v_3$, and:

$$v_3=v_y=18.0 \text{ kN/s} \quad (6)$$

$$v_1=2\times v_3/10=3.6(kN/s) \quad (7)$$

$$v_2=(2+3)\times v_3/10=9.0(kN/s) \quad (8)$$

Assuming the maximum acceleration of the initial first, second, and third stages are respectively $a_{max1}$, $a_{max2}$, and $a_{max3}$, then:

$$v_1=v_0+a_{max1}\times t_{c1} \quad (9)$$

$$v_2=v_1+a_{max2}\times t_{c2} \quad (10)$$

$$v_3=v_2+a_{max3}\times t_{c3} \quad (11)$$

Substituting $v_0 = 0$ and the above first equation into the seventh equation and sorting, so as to obtain:

$$a_{max1}=\frac{v_1}{t_{c1}}=\frac{3.6}{100}=0.036(kN/s^2)=36(N/s^2) \quad (12)$$

Similarly:

$$a_{max2}=\frac{v_2-v_1}{t_{c2}}=\frac{9.0-3.6}{60}=0.09(kN/s^2)=90(N/s^2) \quad (13)$$

$$a_{max3}=\frac{v_1-v_2}{t_{c3}}=\frac{18-9.0}{40}=0.225(kN/s^2)=225(N/s^2) \quad (14)$$

Second Embodiment

The controlled object of the control method for advance prevention of the hydraulic impact is the strain:

A 30 ton electrohydraulic servo universal testing machine. The minimum control frequency of the system ($f_{min}$) is 150 Hz. The strain velocity of the request loading of the tension test is 6 µε/s. The maximum valve opening is 40000. The testing machine will be suspended and the load and strain volume will be reset after the testing machine starts and the cylinder arrives a suitable position. When a regular hydraulic test starts, the automatic conversion program will be launched first, so as to ensure the slow loading of the cylinder. The valve opening of the initial loading controlled by the to computer is 1000. When the load is 100N, the system of testing machine will automatically switch to that the strain speed of the actual loading (v) to be equal to the strain speed of the request loading ($v_y$), simultaneously satisfy that the acceleration of the actual loading (a) is lower than or equal to the maximum acceleration ($a_{max}$), set the initial velocity of the cylinder ($v_0$) to be equal to 0 and the factor of the initial period for loading of the hydraulic system (k) to be equal to 22500 second, and utilize two speed 20/80 incremental control on the maximum acceleration of the hydraulic system.

According to the above test conditions, because the minimum control frequency period ($T_{min}$) is:

$$T_{min} = 1/f_{min}(s) \qquad (1)$$

the initial period for loading ($t_c$) of the hydraulic system is:

$$t_c = k \times T_{min} = k \times (1/f_{min}) = k/f_{min} = 22500/150 = 150(s) \qquad (2)$$

Assuming that under the uniform acceleration of the hydraulic system, the initial first and second time periods are respectively $tc_1$ and $tc_2$, then:

$$t_{c1} = t_c \times 8/10 = 150 \times 8/10 = 120(s) \qquad (3)$$

$$t_{c2} = t_c \times 2/10 = 150 \times 2/10 = 30(s) \qquad (4)$$

Assuming the final speed of the initial first and second stages are respectively $v_1$ and $v_2$, and:

$$v_2 = v_y = 6 \ \mu\varepsilon/s \qquad (5)$$

$$v_1 = v_2 \times 2/10 = 1.2 (\mu\varepsilon/s) \qquad (6)$$

Assuming the maximum acceleration of the initial first and second stages are respectively $a_{max1}$ and $a_{max2}$, then:

$$v_1 = v_0 + a_{max1} \times t_{c1} \qquad (7)$$

$$v_2 = v_1 + a_{max2} \times t_{c2} \qquad (8)$$

Substituting $v_0=0$ and the above first equation into the fifth equation and sorting, so as to obtain:

$$a_{max1} = \frac{v_1}{t_{c1}} = \frac{1.2}{120} = 0.01(\mu\varepsilon/s^2) \qquad (9)$$

Similarly:

$$a_{max2} = \frac{v_2 - v_1}{t_{c2}} = \frac{6 - 1.2}{30} = 0.16(\mu\varepsilon/s^2) \qquad (10)$$

Third Embodiment

As first embodiment: a 500 ton electrohydraulic servo pressure testing machine. The control frequency of the system ($f_{min}$) is 150 Hz. The loading speed required by the test ($v_y$) is 18.0 kN/s. The maximum valve opening is 30000. The testing machine will be suspended and the load will be reset after the testing machine starts and the cylinder arrives the position where the test item is 2 mm from the top board. When a regular hydraulic test starts, the automatic conversion program will be launched first, so as to ensure slow loading of the cylinder. The valve opening of the initial loading controlled by the computer is 1000. When the load is 1000N, the computer controlled system will automatically switch to that the velocity of the actual loading (v) to be equal to loading speed required by the test ($v_y$), simultaneously satisfy that the acceleration of the actual loading (a) is lower than or equal to the maximum acceleration ($a_{max}$), set the initial velocity of the cylinder ($v_0$) to be equal to 0 and the factor of the initial period for loading of the hydraulic system (k) to be equal to 30000, and utilize three speed 20/30/50 incremental control on the maximum acceleration of the hydraulic system ($a_{max}$).

On the basis of conventional hydraulic testing system, the conventional data processing system is turned into high-frequency data processing system and a dynamic measuring system is added. The frequency of conventional data processing system ($f_1$) is equal to 600 Hz, while the frequency of a high-frequency data processing system ($f_2$) is equal to 20 kHz. Because static measuring system has better stability and higher accuracy then dynamic measuring system in low frequency, part of the data of the static measuring system will be processed by the high-frequency data processing system and converted into input signals of the executive system.

When signal sent out at a certain moment of the initial first stage comprises actual acceleration $a_1=90(N/s^2)$ and actual loading velocity $v_{10}==3.0$ kN/s:

The frequency period of conventional data processing system, T1, is:

$$T_1 = 1/f_1 = 1/600(s) \approx 1.67(ms)(1) \qquad (1)$$

The frequency period of high-frequency data processing system, T2, is:

$$T_2 = 1/f_2 = 1/20000(s) = 0.05(ms) = 50(\mu s)(2) \qquad (2)$$

Hence, the high-frequency data processing system is faster than conventional data processing system by:

$$\Delta T = T_1 - T_2 = 1/600 - 1/20000 = 194/1200 \ (s) \approx 1.62 \ (ms) \qquad (3)$$

Because the frequencies of the high-frequency data processing system and conventional data processing system are different, the theoretical error $\Delta f$ of the applied load of the electrohydraulic servo pressure testing machine is:

$$\Delta f = \qquad (4)$$
$$f_1 - f_2 = (v_{10} * T_1 + (1/2) * a_1 * T_1^2) - (v_{10} * T_2 + (1/2) * a_1 * T_2^2) =$$
$$(3000/600 + 1/2 * 90 * (1/600)^2) -$$
$$(3000/20000 + 1/2 * 90 * (1/20000)^2) \approx 4.85 \ (N)$$

That is to say, the error of applied load of the high-frequency data processing system is lower than it of the conventional data processing system by 4.85N. Hence, contrasting to using conventional data processing system, using high-frequency data processing system will have a smoother curve of applied load.

In a comprehensive control method of the same-time-domain multi-frequency band hydraulic testing system according to the present invention, the controlled object for dealing with the hydraulic impact instantly generated in the hydraulic testing system under sudden speed change or reversal can be load, strain, or shift.

The embodiments of the present invention illustrated above are just preferred implementations of the present invention that shall not limit the protection scope of the present invention. Therefore, every alteration, modification, substitution, combination, or simplification within the technical features of the present invention shall be equivalent substitute mode and shall be covered by the protection scope of the present invention.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A same-time-domain multi-frequency band hydraulic system, comprising:
   a high-frequency data processing system,
   a control system connecting to the high-frequency data processing system for controlling and adjusting a pressure, a current capacity and a direction of a fluid in a hydraulic system,
   an executive system connecting to the control system for converting a pressure energy of the fluid to a mechanism energy,
   a load connecting to the executive system, wherein the load is driven by the executive system,
   a static measuring system connecting the load and the high-frequency data processing system for measuring a response of the hydraulic system and generating a first data, and
   a dynamic measuring system connecting the load and the high-frequency data processing system for measuring a response of the hydraulic system and generating a second data,
   wherein said high-frequency data processing system processes input command signals, the second data from said dynamic measuring system, and the first data from said static measuring system, wherein the high-frequency data processing system further automatically generates, displays, and saves same-time-domain multi-frequency band test result data, wherein part of input signals are converted into input signals of said control system by said high-frequency data processing system and executed by said executive system, wherein the frequency response and measurement accuracy of said dynamic measuring system and said high-frequency data processing system meet the requirements of both the test and the hydraulic testing system.

2. A control method utilizing same-time-domain multi-frequency band hydraulic system to conduct hydraulic test, comprising the steps executed by a computer of:
   (1) setting up a factor of an initial period for loading (k) of the hydraulic system and calculating the initial period for loading ($t_c$) of the hydraulic system according to an operating performance of the hydraulic testing system, a loading speed required by a test ($v_y$), and a control frequency of the hydraulic system ($f_{min}$), wherein k is a positive integer greater than or equal to 2;
   (2) calculating the maximum acceleration ($a_{max}$) of the initial loading based on the loading speed required by the test ($v_y$) and the initial period for loading ($t_c$) of the hydraulic system in said step (1), wherein regarding the loading speed required by the test ($v_y$) and the maximum acceleration ($a_{max}$), during the loading process of the hydraulic test, the hydraulic system simultaneously satisfies that the actual loading velocity (v) is equal to the loading speed required by the test ($v_y$) and that the actual loading acceleration (a) is less than or equal to the maximum acceleration ($a_{max}$); and
   (3) applying the loading way of segment increment to the maximum acceleration ($a_{max}$) in the initial loading phase of the hydraulic system, wherein the number of segment (i) is a positive integer of 2 or 3, wherein the actual loading velocity ($v_i$) that controls a phase is equal to the loading speed required by the phase ($v_{yi}$), wherein the actual loading acceleration ($a_i$) is less than or equal to the maximum acceleration of that phase ($a_{maxi}$) to eliminate an occurrence of hydraulic impact.

* * * * *